United States Patent [19]
Kondo

[11] Patent Number: 5,746,696
[45] Date of Patent: May 5, 1998

[54] FLEXIBLE SHEATHING TUBE CONSTRUCTION

[75] Inventor: Mituo Kondo, Omiya, Japan

[73] Assignee: Fuji Photo Optical Co., Ltd., Omiya, Japan

[21] Appl. No.: 636,265

[22] Filed: Apr. 24, 1996

[30] Foreign Application Priority Data

May 16, 1995 [JP] Japan .................................. 7-140060

[51] Int. Cl.$^6$ ........................................................ A61B 1/00
[52] U.S. Cl. ........................... 600/139; 600/140; 600/144
[58] Field of Search ........................................ 600/139, 140, 600/141, 143, 144; 138/120, 141, 142, 177; 604/280, 282, 264

[56] References Cited

U.S. PATENT DOCUMENTS

| | | | |
|---|---|---|---|
| 3,131,726 | 5/1964 | Van Sciver, II et al. | 138/142 |
| 3,739,770 | 6/1973 | Mori | 600/139 |
| 4,327,711 | 5/1982 | Takagi | 600/139 |
| 5,137,013 | 8/1992 | Chiba et al. | 128/4 |

Primary Examiner—Beverly M. Flanagan
Attorney, Agent, or Firm—Oblon, Spivak, McClelland, Maier & Neustadt, P.C.

[57] ABSTRACT

A flexible sheathing tube particularly suitable for use on an endoscopic insertion rod or flexible light guide cable, the sheathing tube having a laminated wall basically including a helical coil as a flexible base structure and a tubular metal wire netting placed around the helical coil member. The helical coil member has a certain number of helices thereof tightly closed and fixed to each other into the form of a rigid ring at least at one end of the sheathing tube to be trimmed in a subsequent stage. The end ring provides a rigid support uniformly on and around the inner periphery of the tubular netting, permitting a cutter blade to cut the end of the sheathing tube to a predetermined length by a straight clear cut through the laminated wall and the backing end ring. Accordingly, flexible component parts which are received in the sheathing tube are free from damages as caused by metal wires of the tubular netting which would otherwise be unraveled and deformed to protrude inward of the sheathing tube at the time of an end trimming operation.

5 Claims, 4 Drawing Sheets

FLEXIBLE SHEATHING TUBE CONSTRUCTION

BACKGROUND OF THE INVENTION

1. Field of the Art

This invention relates to a flexible sheathing tube construction particularly suitable for use on endoscopic insertion rods, endoscopic light guide cables and the like.

2. Prior Art

As shown in FIG. 1, in most cases, endoscopes which are currently in wide use in medical and industrial fields are largely constituted by a manipulating head assembly 2 with manipulating control means necessary for endoscopic observation, a flexible insertion rod member 1 extended out on the front side of the manipulating head assembly 2 for insertion into an internal region of human body or machine to be inspected, and a flexible light guide cable 3 extended out on the rear side of the manipulating head assembly 2 for connecting the endoscope to a light source (not shown). The insertion rod 1 is mostly constituted by a flexible rod section 1a, which occupies substantially the entire length of the insertion rod from a proximal end connected to the manipulating head assembly 2, except a relatively short angle section 1b and a rigid tip end section 1c which are successively connected to the fore end of the flexible rod section 1a. The light guide cable 3 is arranged similarly to the flexible rod section 1a in basic construction.

Of the three sections of the endoscopic insertion rod 1, the flexible rod section 1a is normally provided in a quite lengthy form because it needs to have a length which is sufficient for reaching an internal region to be examined and at the same time for keeping an operator away from a patient by a distance which can ensure unobstructed operations on various control means on the manipulating head assembly 2. In order to be bendable along a path of insertion, the flexible rod section 1a is normally arranged to have a high degree of flexibility along almost the entire length thereof. More particularly, the flexible rod section 1a needs to have satisfactory flexibility in bending directions but should have sufficient strength against forces acting to stretch, compress or crush the rod in axial or radial directions.

The flexible rod section 1a of the endoscopic insertion rod 1 usually contains a light guide, an image guide (or a signal cable in case of an electronic endoscope), a biopsy channel and an air/water feed pipe which are coextensively fitted within a flexible sheathing tube. These fitted components are formed of a flexible material to ensure that the rod section 1a is bendable in arbitrary directions along a path of insertion which may contain turns and bends within its length. Shown in FIG. 2 is a flexible sheathing tube construction which is generally used for the endoscopic flexible rod section 1a, namely, a flexible sheathing tube 10 having a layer of tubular netting 12 and an outer skin layer 13 successively laminated on inner and outer helical coil members 11a and 11b. The helical coil members 11a and 11b, which constitute a basic flexible structure for the flexible sheathing tube 10, are each formed by helically winding a metal strip of stainless steel or the like in a predetermined pitch. The tubular netting 12, of metal wire mesh of predetermined mesh size and weave design, provides a base for laminating the outer skin layer 13 by extrusion molding or other suitable means after application of an adhesive. Attached to an end of the flexible sheathing tube 10 is a joint ring 14 which connects the flexible sheathing tube 10 to an adjoining section of the endoscopic insertion rod, for example, to the afore-mentioned angle section 1b.

The flexible light guide cable 3 which connects the manipulating head assembly 2 to a light source usually employs a flexible sheathing tube of a similar construction because it also needs to be flexible in bending directions. Although no biopsy channel exists within the flexible light guide cable, it has at least a light guide and an air/water feed pipe coextensively passed therethrough.

In the fabrication of a flexible sheathing tube of the sort as described above, firstly the inner and outer helical coil members 11a and 11b are formed to provide a basic flexible structure, followed by lamination thereon of the tubular wire mesh netting 12. In so doing, it has been the usual practice to form a netting layer of a slightly longer size and to trim the ends of the laminated netting layer flush with the ends of the helical coil members 11a and 11b. In order to enable a cutter to trim an end of the metal wire netting smoothly and sharply by a straight clear cut in the end trimming stage, metal wires in a trimming end portion of the tubular netting 12, containing a predetermined cutting line, are set by the use of solder.

When trimming an end of the tubular netting 12 on a cutter, metal wires of the tubular netting 12 are subjected to radially inward cutting forces no matter whether they are set with solder. As long as either the helical coil member 11a or 11b exists under the tubular netting 12 along a cutting line, there is little possibility of the tubular netting 12 being deformed by the cutting force in an inward direction. However, the helical coil members 11a and 11b, which are helically wound in a predetermined open pitch, partially contain open spaces between intersecting helices as indicated at A in FIG. 2. Therefore, at such open spaces, the overlying tubular netting 12 is very likely to be pushed and deformed inward by a cutter blade, causing metal wires of the netting 12 to be bent forcibly in radially inward directions, exposing sharply cut metal wire ends P on the inner side of the flexible tube as shown in FIG. 3. Needless to say, these sharply cut ends of metal wires have possibilities of contacting and damaging the flexible component parts of the endoscope, such as light guide, image guide or signal cable, biopsy channel or air/water feed pipe which are fitted in the flexible sheathing tube 10. In order to solve this problem, it is conceivable to conceal the exposed ends of metal wires completely under a protective cover by extending the joint ring at the end of the flexible tube onto the inner periphery of the helical coil members 11a and 11b. However, the extension of the joint ring will result in undesirable restrictions of the internal space of the flexible sheathing tube 10 which has to accommodate a number of component parts of an endoscopic observation system as mentioned above. Therefore, it has been necessitated to remove sharply sticking-out ends of metal wires of the tubular netting 12 manually by the use of a file in an end treatment subsequent to a cutting operation although this is extremely troublesome.

SUMMARY OF THE INVENTION

In view of the foregoing situations, it is an object of the present invention to provide a flexible sheathing tube construction of the sort which has a laminated wall including a tubular metal wire netting fitted around an interstitial tubular flexible structure like a helical coil, and yet which permits trimming an end of the tubular netting flush with the underlying helical coil on a cutter by a straight clear cut, without causing metal wires at a trimmed end of the tubular netting to bend in radially inward directions and protrude into the sheathing tube by deformation under a cutting force.

In accordance with the present invention, the above-stated objective is achieved by the provision of a flexible sheathing tube for use on an endoscope, the sheathing tube having a laminated wall including, from the inner side thereof, a flexible helical coil structure formed by helically winding a metal strip in a predetermined open pitch, a tubular metal wire netting fitted on the helical coil structure, and an outer skin layer laminated on the tubular netting, characterized in that: the helical coil structure is constituted by at least one helical coil member having a number of helices thereof tightly closed and fixed to each other into the form of a rigid ring at least at one end of the sheathing tube to be trimmed in a subsequent stage, the rigid ring providing a solid backing support uniformly on and around the inner periphery of the tubular metal wire netting in such a way as to permit a cutter blade to trim the sheathing tube to a predetermined length by a straight clear cut through the tubular metal wire netting and helical coil member of the laminated wall.

The flexible sheathing tube of an endoscopic insertion rod or of a flexible light guide cable of an endoscope is normally connected to other component parts at the opposite ends thereof. More specifically, in the case of a flexible sheathing tube of an endoscopic insertion rod, it is connected to a manipulating head assembly of the endoscope and to an angle section at its rear and fore ends, respectively. In this regard, for the purpose of providing a secure rigid connection to the adjoining components of the endoscope, the flexible sheathing tube is not necessarily required to have flexibility at these connecting ends. In other words, a number of helices of the coil member at the fore and rear ends of the sheathing tube are not required to be spaced apart in a predetermined pitch as the helices in the remainder part of the sheathing tube. Therefore, according to the flexible sheathing tube construction of the invention, a number of helices are tightly closed and fixed to each other into a rigid ring form at the fore and/or rear end of a coil member (in case the sheathing tube incorporates a single coil member in the tubular flexible structure) or of one of coil members (in case the flexible tube incorporates two or more coil members in the tubular flexible structure). The helices which are closed and fixed in a form of a rigid ring provide a rigid backing support on and around the inner periphery of the overlying tubular netting uniformly in all radial directions as an end portion of the netting is trimmed or cut to a predetermined length by a cutter blade through exertion of a radially inward cutting force on and around the entire circumference of the tubular netting. In the cutting operation, the rigid end ring prevents sharply cut ends of metal wires of the netting from being unraveled and bent inward to stick out within the flexible sheathing tube. It follows that the flexible components which are fitted in the flexible sheathing tube, such as the above-mentioned light guide, image guide, signal cable, biopsy channel, and air/water feed pipe are all maintained in securely protected state free from troubles or damages as would result from contact with sharply cut wire ends of the tubular netting.

The above and other objects, features and advantages of the invention will become apparent from the following particular description of the invention, taken in conjunction with the accompanying drawings which show its preferred embodiments.

DESCRIPTION OF PREFERRED EMBODIMENTS

Now, the invention is described more particularly by way of its preferred embodiments with reference to the accompanying drawings.

Figure 1:
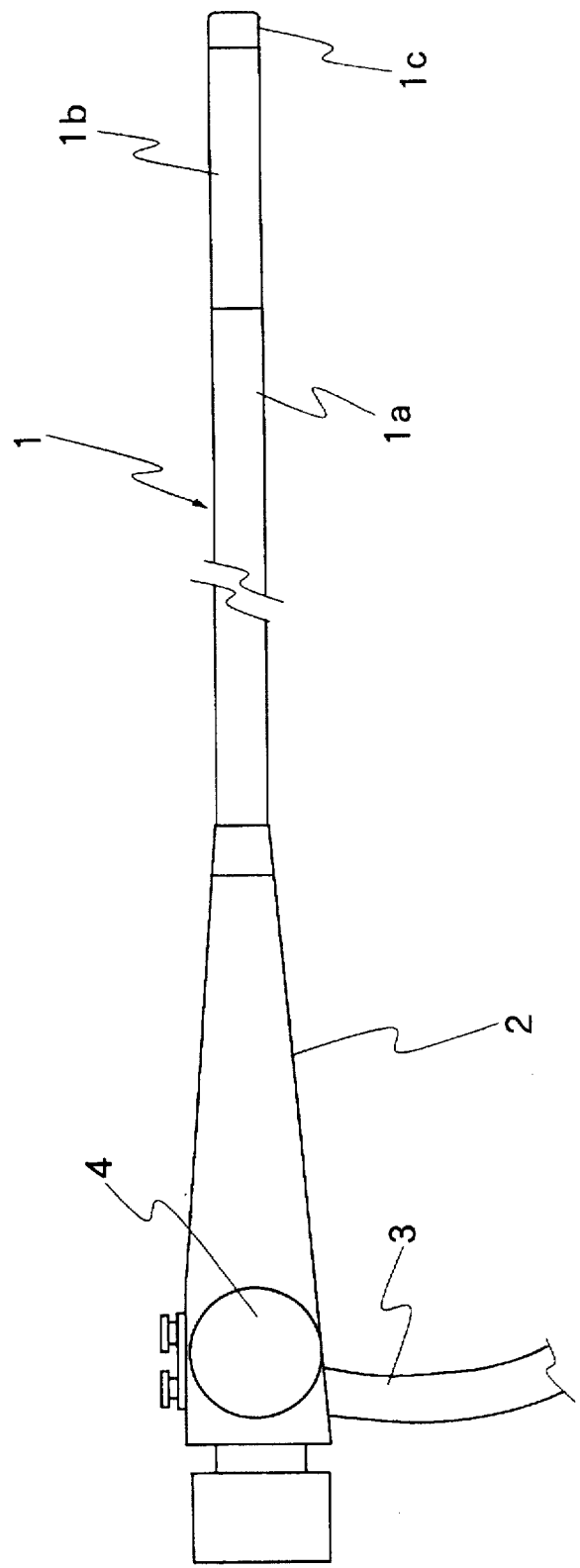
FIG. 1 is a schematic view of an endoscope having a number of endoscopic components sheathed in a flexible tube to form an insertion rod to be introduced into an internal region to be inspected.
Figure 2:
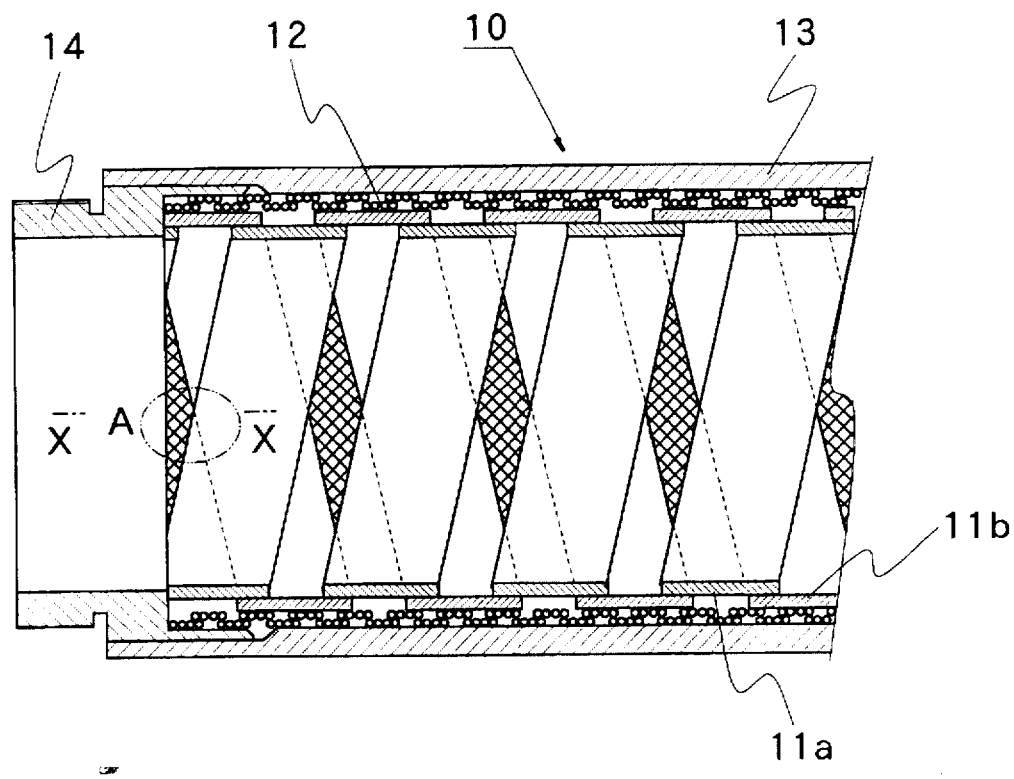
FIG. 2 is a longitudinal sectional view through one end of a flexible sheathing tube of prior art.
Figure 3:
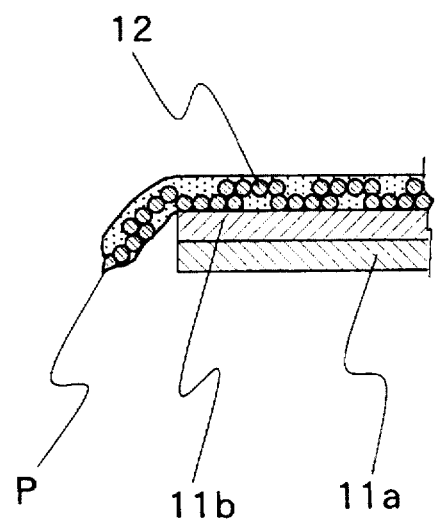
Fig.3 is an enlarged sectional view taken on line X—X of FIG. 2.
Figure 4:
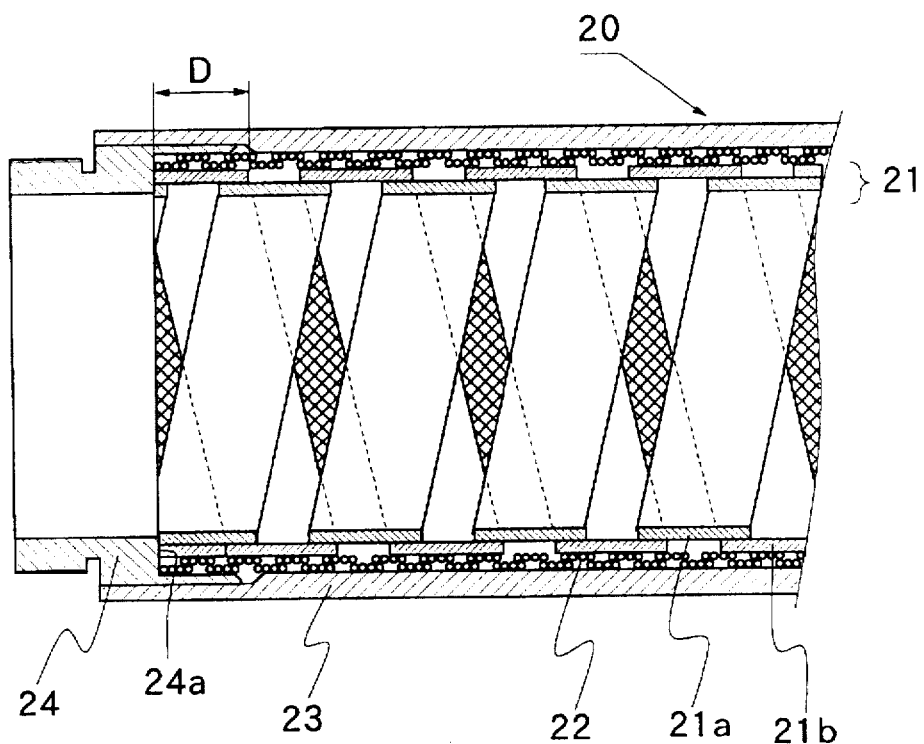
FIG. 4 is a longitudinal sectional view through one end of a flexible sheathing tube according to the invention.

In basic construction, the flexible sheathing tube of the present invention has no differences in particular from the conventional counterpart shown in FIG. 2. Namely, as seen in FIG. 4, a flexible sheathing tube 20 according to the invention basically includes as a flexible base structure a tubular double coil structure 21 constituted by inner and outer helical coil members 21a and 21b, a tubular metal wire netting 22 laminated on the tubular double coil structure 21, and an outer skin layer 23 formed on the tubular netting layer 22 by the use of an extruder or other molding means after application of an adhesive on the netting layer 22. A joint ring 24 is attached to an end of the flexible tube 20.

Of the flexible sheathing tube 20 with the basic construction as described above, the two helical coil members 21a and 21b are constituted by two separate metal strips which are helically wound in a predetermined open pitch and in opposite winding directions relative to each other. However, at or in the vicinity of one end of the flexible tube 20, a number of helices of the outer helical coil member 21b are closed and fixed to each other, forming a rigid end ring which substantially has a width D in the axial direction. This enables a cutter blade to trim the end of the sheathing tube to length by a straight and clear cut through the end ring of the outer helical coil 21b, more particularly, through the inner and outer helical coil members 21a and 21b and through the tubular netting 22 which is rigidly supported on the end ring of the outer helical coil member 21b, severing the tubular metal wire netting 22 flush with the helical coil members 21a and 21b without any possibility of metal wires of the tubular netting being unraveled and deformed inward to protrude into the inner side of the flexible coil structure 21.

Figure 5:
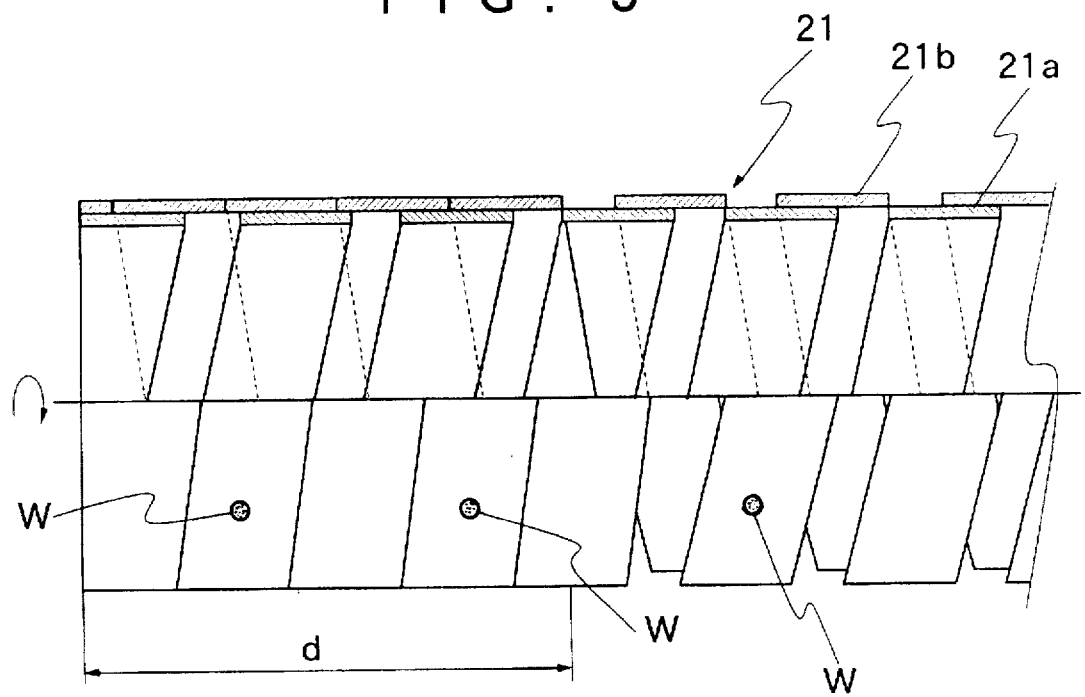
FIG. 5 is a half-sectioned side view of helical coil members.

The flexible sheathing tube 20 of the above construction can be fabricated in the manner as described below. First, the inner and outer helical coil members 21a and 21b are each formed by winding a metal strip helically around a rod-like jig in a predetermined open pitch. After forming the double coil structure 21, a number of helices at one end of the outer helical coil member 21 are closed tightly to each other by applying a torsional force to the end of the coil member 21 as indicated by an arrow in FIG. 5. As a result, one end of the outer helical member 21b is closed into a ring-like form, which substantially has a width (d) in the axial direction depending upon the number of closed helices. In this state, of course, the closed helices tend to return to the original spaced open-pitch positions by resiliency as soon as the torsional force is removed from the outer helical coil member 21b. Therefore, the tightly closed helices are fixed in the ring-like form by laser spot welding, soldering, brazing or other suitable means, securely fixing the closed helices to each other and to underlying helices of the inner helical coil member 21a, preferably at one or several welding spots W which are distributed on the tightly closed helices as well as on at least one open helix immediately ensuing the ring-like closed helices. By so doing, a discretely rigid ring-like structure is fixedly formed by the tightly closed helices at one end of the flexible coil structure.

Figure 6:
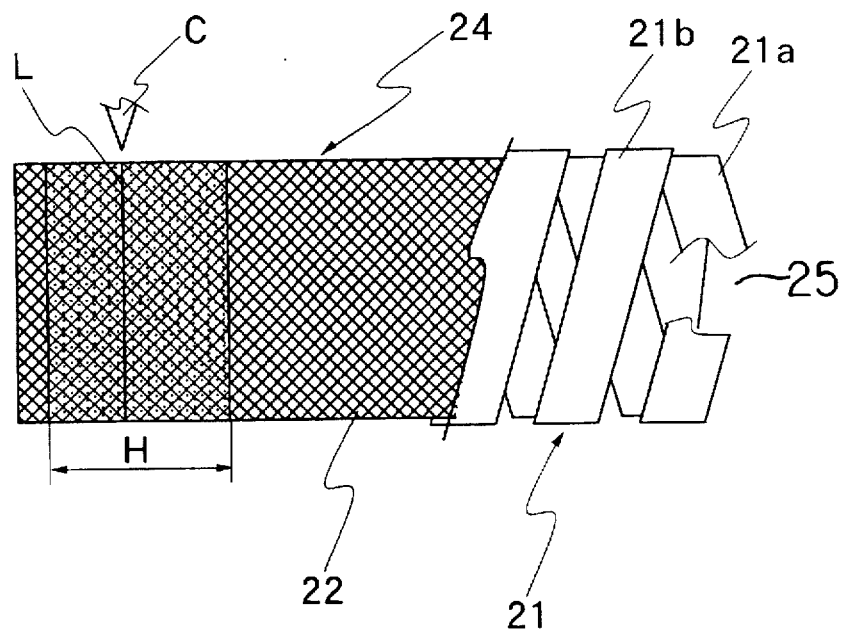
FIG. 6 is a schematic illustration explanatory of a cutting operation on a tubular metal wire netting fitted on the helical coil members.

Next, the tubular netting layer 22 is laminated on the double coil structure 21 by netting or weaving metal wires around the circumference of the coil structure 21. Then, as shown in FIG. 6, an end portion of the tubular netting 22 is set in a firmly fixed state by application of solder H over an area corresponding to the width (d) of the tightly closed helices at one end of the outer helical coil member 21b. The resulting tubular laminated structure 25 consisting of the double coil structure 21 and the tubular netting 22 is trimmed to a predetermined length along a predetermined cutting line L by the use of a cutter C. In this instance, as mentioned hereinbefore, the cutting line L is located to pass through the double coil structure 21 at a point intermediate of the width (d) of the end ring or the tightly closed helices of the outer helical coil member 21b, and through the soldered end portion H of the tubular netting 22. Accordingly, the tubular laminated structure 25 as a whole is set in a rigid state, permitting the cutter blade C to make a clear cut therethrough along a predetermined straight cutting line and thus completely precluding the possibilities of metal wires of the tubular netting being unraveled and forcibly deformed radially inward to protrude into the sheathing tube.

The tubular laminated structure 25 which has been trimmed to a predetermined length by an end trimming operation in this manner is useful, for example, as a flexible sheathing tube of an endoscopic insertion rod. For this purpose, a joint ring 24 is fitted on the trimmed end of the tubular laminated structure 25 for connection thereto of an angle section, bringing a stepped or rising wall portion 24a of the joint ring 24 into abutting engagement with the end of the tubular laminated structure 25. After applying an adhesive around the tubular netting 22, an outer skin layer 23 is formed thereon by extrusion molding or other suitable means. In so doing, the end of the tubular netting 22 can be held in intimate contact with the stepped wall portion 24a since it has been trimmed by a straight cut flush with the end of the double coil structure 21 as described above, precluding possibilities of metal wires of the tubular netting 22 unraveling and protruding inward of the joint portion.

The flexible component parts of an endoscopic observation system, which are fitted in the flexible sheathing tube of the above construction, such as a light guide, an image guide or a signal cable, a biopsy channel and an air/water feed pipe are not set in fixed positions, namely, are all allowed to move in arbitrary directions within a certain delimited range while the endoscope is being used for an internal examination. However, since the end of the tubular netting 22 has been trimmed flush with the underlying coil structure 21 by a clear straight cut as described above, these fitted component parts are completely freed from damages as caused by contact with sharply cut ends of metal wires of the tubular netting 22 which might otherwise happen to protrude into the flexible tube at or in the vicinity of the joint ring 24. Thus, the flexible sheathing tube of the invention can securely protect the fitted component parts which are formed of a flexible vulnerable material.

For use on an endoscopic insertion rod, the sheathing tube is required to have satisfactory flexibility in bending directions. In this regard, at an end where the flexible tube is rigidly connected to an angle section or other section of an endoscopic insertion rod by way of a rigid joint member like the above-described joint ring 24, however, the endoscopic insertion rod is not expected to have bending flexibility. Therefore, the end ring which is formed by tightly closing a certain number of helices at the joint end of the outer helical coil member 21b will not cause any trouble in particular. Nevertheless, the ring of closed helices would impair the flexibility of the insertion rod should it have a width greater than the joint ring 24 in the axial direction. Accordingly, it is preferable that the end ring of closed helices be restricted to a coil end portion which lies under the joint ring 24.

Figure 7:
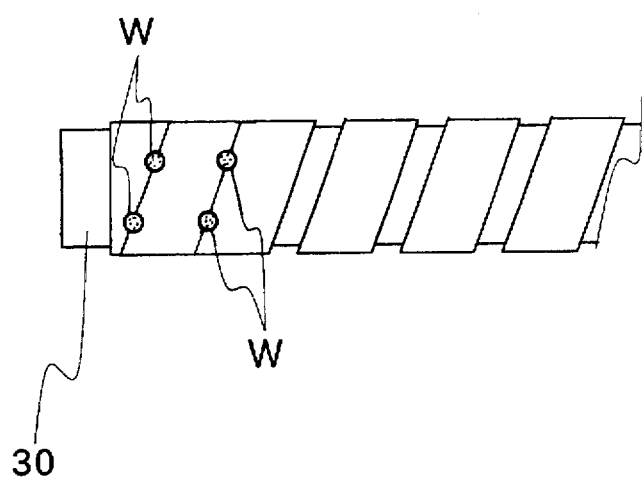
FIG. 7 is a schematic illustration explanatory of an operation of closing and fixing a number of helices to each other at one end of a helical coil member in another embodiment of the invention employing only one helical coil layer in a flexible base structure.

In the above-described embodiment of the invention, a rigid ring structure is formed by tightly closing and fixing a number of helices at one end of the outer helical coil member 21b which constitutes the double coil structure 21 along with the inner helical coil member 21a. However, a similar rigid end ring can be formed by closing a number of helices at one end of the inner helical coil member 21a or of both of the inner and outer helical coil members 21a and 21b. In case the flexible coil structure consists of a single helical coil member, a helical coil 31 is firstly formed around a rod-like jig 30 as shown in FIG. 7, and a rigid end ring is formed at one end of the coil 31 by tightly closing and securely fixing a number of helices to each other by spot welding W at a number of positions along a helical seam line between closed helices. In the same manner as in the foregoing embodiment, a tubular netting is then woven around the circumference of the coil structure 31, followed by setting of the netting layer with solder and end trimming by a cut through the end ring. Further, the flexible sheathing tube construction has been described in connection with a joint construction between an endoscopic flexible insertion rod and an angle section, it can be similarly applied to the rear end of the endoscopic insertion rod to be connected to a manipulating head assembly of an endoscope or to a flexible light guide cable of an endoscope to be disconnectibly connected to a light source through an optical connector.

As clear from the foregoing description, this invention concerns a flexible sheathing tube construction with a laminated wall which basically includes a helical coil as a flexible base structure and a tubular metal wire netting placed around the helical coil structure. A number of helices of the helical coil are tightly closed and fixed to each other to form a rigid end ring at least at one end of the sheathing tube to be trimmed in a subsequent stage, where the end ring provides a rigid support uniformly on and around the inner periphery of the tubular netting, permitting a cutter blade to trim the sheathing tube to a predetermined length by a straight clear cut through the tubular netting of the laminated wall. Accordingly, the sheathing tube accommodates flexible components of an endoscope in a securely protected state, free from damages as would be caused by metal wires of the tubular netting which might otherwise be unraveled and deformed to protrude inward of the sheathing tube under the force of a cutter blade during an end trimming operation.

What is claimed is:

1. A flexible sheathing tube for use on an endoscope, said sheathing tube having a laminated wall including, from the inner side thereof, a flexible helical coil structure formed by helically winding a metal strip in a predetermined open pitch, a tubular metal wire netting fitted on said helical coil structure, and an outer skin layer laminated on said tubular netting, characterized in that:

said helical coil structure is constituted by at least one helical coil member having a number of helices thereof tightly closed and fixed to each other into the form of a rigid ring at least at one end of said sheathing tube to be trimmed in a subsequent stage, said rigid ring providing a solid backing support uniformly on and around the inner periphery of said tubular metal wire netting in such a way as to permit a cutter blade to trim said sheathing tube to a predetermined length by a straight clear cut through said tubular metal wire netting and helical coil member of said laminated wall.

2. A flexible sheathing tube as defined in claim 1, wherein said helical coil structure is constituted by a couple of superposed helical coil members of opposite winding directions, at least one of said helical coil members having a number of helices tightly closed and fixed to each other into the form of a rigid ring at one end of said sheathing tube to be trimmed in a subsequent stage, closed helices of said one helical coil member being securely fixed to helices of the other helical coil member.

3. A flexible sheathing tube as defined in claim 1, wherein said flexible coil structure comprises a single helical coil member having a plurality of helices thereof tightly closed and fixed to each other into the form of a rigid ring at one end of said sheathing tube to be trimmed in a subsequent stage, closed helices of said helical coil member being securely fixed to each other along a helical seam line between closed helices.

4. A flexible sheathing tube according to any one of claims 1 to 3, wherein closed helices of said coil member are set in a ring-like form by means of laser spot welding.

5. A flexible sheathing tube according to any one of claims 1 to 3, wherein said tubular wire metal netting is set with solder in areas overlying said closed helices of said coil member.

* * * * *